United States Patent [19]

Schmidt-Dunker et al.

[11] 4,086,334

[45] Apr. 25, 1978

[54] COMPOSITION AND METHOD FOR THE TREATMENT OF DISORDERS OF CALCIUM METABOLISM

[75] Inventors: Manfred Schmidt-Dunker, Düsseldorf; Matthias Potokar, Heiligenhaus, both of Germany

[73] Assignee: Henkel Kommanditgesellschaft Auf Aktien, Düsseldorf-Holthausen, Germany

[21] Appl. No.: 745,838

[22] Filed: Nov. 29, 1976

[30] Foreign Application Priority Data

Dec. 1, 1975  Germany ........................... 2553963
Dec. 1, 1975  Germany ........................... 2553962
Dec. 1, 1975  Germany ........................... 2553964

[51] Int. Cl.$^2$ .................... A61K 37/00; C07C 103/52
[52] U.S. Cl. ............................. 424/177; 260/112.5 T
[58] Field of Search .............. 260/112.5 R, 112.5 T; 424/177

[56] References Cited

PUBLICATIONS

W. A. Crosbie, et al.; Chem. Abst. 83, 1975, pp. 126795v.
J. B. Lesh, et al.; Chem. Abst. 82, 1975, pp. 81080u.
P. Bergmann, et al.; Chem. Abst. 82, 1975, pp. 168567g.
F. R. Singer, et al.; Chem. Abst. 82, 1975, pp. 68689e.
C. Gennari, et al.; Chem. Abst. 83, 1975, pp. 1297c.
J. C. Benier, et al.; Chem. Abst. 84, 1976, pp. 130798m.
C. Genari, et al.; Chem. Abst. 84, 1976, pp. 54606e.
N. A. Samaan, et al.; Chem. Abst. 81, 1974, pp. 100029g.
A. Caniggia, et al.; Chem. Abst. 83, 1975, pp. 1296b.

*Primary Examiner*—Delbert R. Phillips
*Attorney, Agent, or Firm*—Hammond & Littell

[57] ABSTRACT

The water-soluble calcitonins and the water-soluble pharmaceutically-acceptable compounds of acidic nature which are effective against Paget's disease and which contain at least two acidic groups separated by not more than two carbon atoms act synergistically in inhibiting a pathological increased calcium metabolism rate (including the solubilization of bone calcium which occurs in Paget's disease). The components in combination, when administered in respectively preferred amounts, inhibit or arrest loss of calcium by the bones of the body with less severe side effects than those caused by equivalent therapeutic doses of the calcitonin alone or by equivalent therapeutic doses of the compounds of acidic nature alone.

28 Claims, No Drawings

COMPOSITION AND METHOD FOR THE TREATMENT OF DISORDERS OF CALCIUM METABOLISM

FIELD OF THE INVENTION

The present invention relates to compositions for inhibiting a pathological increased calcium metabolism rate as shown during Paget's disease (morbus Paget, osteodystrophia deformans), hypercalcemia and osteoporosis. The invention includes the compositions themselves in dry and dissolved bulk and unit dose state, methods for the preparation of the compositions, and the treatment of the above-mentioned diseases with those materials administered together or separately. The invention further includes a sterile package containing the components in forms suitable for dosing.

BACKGROUND OF THE INVENTION

Paget's disease causes a change in the composition and structure of the affected bones and results in their deformation. The disease appears in circumscribed areas and can affect one or a number of bones. It affects particularly frequently the bones of the sacrum, pelvis, femur, tibia, and the vault of the cranium.

In Paget's disease the dimensions of the affected bone or bones increase about 10-fold and newly formed bone possesses a faulty structure and is undermineralized (i.e., it contains an insufficient proportion of calcium and similar elements). The increased volume of the bone can destroy adjacent nerves and blood vessels, and the low mineral content of the bone frequently leads to their undergoing spontaneous fracture (i.e., a fracturing which has no evident cause). Osteosarcomas frequently have their site in a locus which is affected by Paget's disease.

In hypercalcemia, increased solubilization of calcium in bones frequently occurs in combination with a reduction in the amount of calcium secreted by the kidneys, and both these events lead to an increase of the calcium level in the blood serum of the mammal affected. The causes of this disease (hypercalcemia) have been ascribed to an increased sensitivity to vitamin D or to substances like vitamin-D which are produced in tumors (paraneoplastic syndrome). The symptoms of hypercalcemia have also been found in primary or secondary hyperparathyreoidism or in tumors (in many instances carcinomas) which secrete parathormone-like substances. Plasmacytomas or an estrogeninduced hypercalcemia are also possible.

Osteoporosis is one of the most frequent disorders resulting from faulty bone metabolism (i.e., catabolism), and is characterized by a loss of bone substance, the bone otherwise remaining unchanged in composition. The disease is observed in mammals in general. In men, loss of bone substance generally starts at the ages of 40 to 50, and in women it occurs particularly frequently after menopause. Disorders in the hormone balance are frequently assumed to be the cause. But non-hormal factors, e.g. the immobility of extremities and food or medicine-related factors cannot be excluded from the genesis of osteoporosis.

The loss of bone substance, measured as a percentage of the total calcium of the body before onset of the disease, can amount to 30%. Thinning of the cortical bones, as well as conversion of the bone to a spongy porous structure leads more frequently with increasing age to spontaneous fractures.

Up to the present, treatments of the above-mentioned bone diseases have been unsatisfactory. Attempts were made to slow down degradation or alteration of the bones by administration of corticoids and salicylates, but it was found that effective doses of these medicaments led rapidly to undesired side effects. Indomethacin, phenylbutazone and substances which stimulate the circulation provided temporary relief to the patient, but they had no effect on the progress of the disease. Treatments with sodium fluoride produced visible results only in a few cases.

In the last few years two new therapies were found which provided better results, particularly in Paget's disease. The hormone calcitonin, (also termed "thyrocalcitonin") which is responsible in the organism of mammals (including humans), together with Parathormone (i.e., the parathyroid hormone) for calcium homeostasis and which is formed in the parafollicular cells of the thyroid gland was found to have a definite efficacy. Calcitonin itself is a polypeptide hormone composed of 32 amino acid units. This material, as well as several animal analogs (of salmon, pig and cattle), and their synthetic analogs (hereinafter termed "calcitonins") possess the property of decreasing the level of ionic calcium ($Ca^{2+}$) in the blood serum rapidly; they also possess the property of causing dissolved calcium to be absorbed or to be reabsorbed by the bone. Prolonged treatment with human calcitonin, and particularly with its synthetic and animal produced analogs, presents the danger of causing undesirable formation of antibodies and a resulting incompatibility. In addition, therapy with calcitonin does not result in a complete regression of the principal symptoms of Paget's disease, e.g. the increase in the alkaline phosphatase level in the blood serum and the increase in the secretion of hydroxyproline in the urine.

Another therapy of the above-described disorders of bone metabolism in man and other mammals is based on the administration of certain water-soluble diphosphonic compounds and other acidic compounds. These substances act primarily on the mineral phase of the bone and decrease the crystallization of apatite and the solubility of the bone materials. In addition, they appear to provide sites for absorption of the soluble calcium ions in the blood. The latter effect is based on a strong chemisorption of these compounds on the surface of calciferous minerals like apatite. These compounds contain at least two acidic substituents (e.g. phosphono, carboxy and sulfo) separated by not more than two carbon atoms, and come from the group consisting of the water-soluble aminophosphonic acids, the water-soluble amidophosphonic acids, the water-soluble carboxyphosphonic acids, cyclohexanehexacarboxylic acid, and the water-soluble salts thereof.

The increased rate of degenerative bone metabolism can be decreased by oral administration of these acidic inhibitors. Good results are obtained particularly in controlling Paget's disease. Hypercalcemia is also decreased, and osteoporosis of the bones undergoes reversal.

Though these compounds are more effective than calcitonin, prolonged therapy therewith has been found to provide undesired side effects. Not only is the rate of dissolution of the bone minerals decreased, but mineralization of the bones is inhibited, the number of unmineralized osteoplasts increases, and an increase in the number of osteo disorders occurs when large doses are administered.

DESCRIPTION OF THE INVENTION

The discovery has now been made that a combination of the therapy of administration of the calcitonins and certain pharmaceutically-acceptable aminophosphonic acids, amidophosphonic acids, carboxyphosphonates and cyclohexanehexacarboxylic acids (and their pharmaceutically-acceptable water-soluble salts), as more particularly stated above, when employed together as treating agents against the diseases mentioned, provide very satisfactory therapeutic results; i.e., the combination arrests the diseases or decreases their severity, while causing less severe side reactions, with substantially decreased dosages. The components therefore appear to interact synergistically. The invention appears to be generally applicable to combinations of the calcitonins with water-soluble pharmaceutically acceptable compounds containing at least two acidic substituents separated by not more than two carbon atoms.

The invention thus combines the advantages of the two individual therapies without incorporating their disadvantages. The decrease of the calcitonin dose greatly decreases the danger of the formation of antibodies. The decrease of the dose of the acid component (the aminophosphonic acids, amidophosphonic acids, cyclohexane hexacarboxylic acids, and the pharmacologically harmless watersoluble salts of these acids) leads in Paget's disease to a clear decrease in the content of alkaline phosphatases in blood serum and in the content of hydroxyproline in the urine, without the formation of visible osteoid borders. The general tolerability of the therapeutically effective doses of the combination of agents (even when they are administered separately, by different routes) is much better than that of each of the agents administered singly in therapeutically effective amounts. The treatment can thus be continued over a longer period of time, and undesired side effects are at a low level.

The compositions of the present invention thus comprise (A) a water-soluble calcitonin and (B) a water-soluble pharmaceutically acceptable adjuvant organic compound which is effective against Paget's disease which contains at least two acidic groups separated by not more than two carbon atoms and which is selected from the group consisting of the water-soluble aminophosphonic acids, the amidophosphonic acids, the carboxyphosphonic acids, cyclohexane-hexacarboxylic acid, and the water-soluble salts thereof, the ratio of (A) to (B) being from 1:10 to 10:1, if the amount of (A) is expressed in MRC units and (B) in mg. Two or more of the organic acidic compounds can be present.

The composition can be present in a single injectible solution in a pharmaceutically acceptable injectable liquid, which, if desired, can be present in emulsified state in a pharmaceutically acceptable oil to retard the absorption time. If desired, the composition can be present in unit dose form.

The adjuvant can be prepared for unit dose administration as a compressed tablet or dragee, or can be prepared as an encapsulated loose powder.

In numerous instances no need will be found to administer the calcitonin more than once a day, but it will often be found desirable to administer the adjuvant as many as four times a day. Accordingly, the invention includes a hermetically sealed, sterile daily dose package for dosing a mammal suffering from pathological increased calcium metabolism, which comprises at least one sterile ampoule containing calcitonin in an amount sufficient to supply from 0.01 to 20 international medical research council units per kilogram of body weight and at least one tablet containing between 25 mg. and 400 mg. of a water-soluble adjuvant compound as is described above. With this package it becomes convenient to administer by injection the single daily dose of calcitonin and to administer the adjuvant in uniformally spaced doses orally.

The invention further provides an emulsion in oil of an aqueous solution of the calcitonin and the adjuvant, permitting both to be injected in slowly absorbable form.

The invention further provides a method of inhibiting the pathological increased calcium metabolism in mammals, which comprises administering daily thereto (A) a water-soluble calcitonin and (B) a water-soluble pharmaceutically acceptable organic adjuvant compound, said adjuvant compound containing at least two acidic groups separated by not more than two carbon atoms and being selected from the group consisting of the water-soluble aminophosphonic acids, the water-soluble amidophosphonic acids, the carboxyphosphonic acids, cyclohexanehexacarboxylic acid, and the water-soluble salts thereof, the amount of said calcitonin being sufficient to supply between about 0.01 and 20 Medical Research Council units thereof per kilogram of body weight per day, and the amount of said adjuvant being 1:10 to 10:1 times the amount of said calcitonin, if the amount of calcitonin is expressed in MRC units and the amount of adjuvant in mg.

The new pharmaceutical preparations for the treatment of the above-described disorders of calcium metabolism (i.e., for decreasing the solubilization of bone calcium in mammals) are characterized in that they contain as one active substances a calcitonin and as the other active airstance at least one other active component which acts as adjuvant selected from the aforementioned groups. More particularly, the groups are as follows. (a) Aminophosphonic and amidophosphonic acids of the general formula:

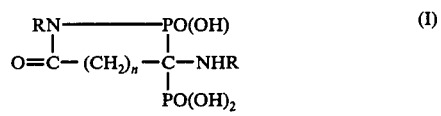

wherein R is a hydrogen atom or $C_{1-6}$ alkyl, and $n$ is 1 to 3;

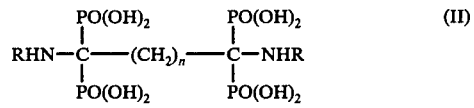

wherein R is H or $C_{1-4}$ alkyl, and $n$ is 1 to 3;

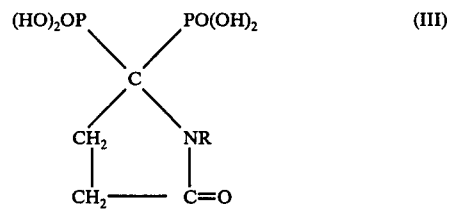

wherein R is H or $C_{1-6}$ alkyl;

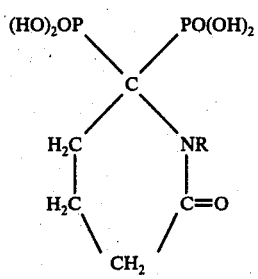

wherein R is H or $C_{1-6}$ alkyl;

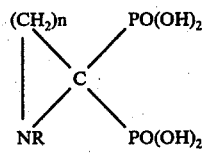

wherein R is H or $C_{1-4}$ alkyl, and $n$ is 3 to 6;

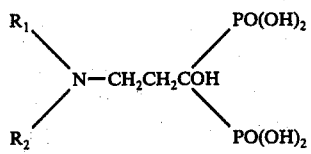

wherein $R_1$ and $R_2$ represent H or $C_{1-3}$ alkyl; (b) carboxyphosphonic acids of the general formula:

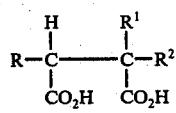

wherein R represents H or a $C_{1-3}$ alkyl, $R_1$ represents $-PO_3H_2$,

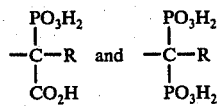

wherein $R_2$ represents H, $C_{1-3}$ alkyl,

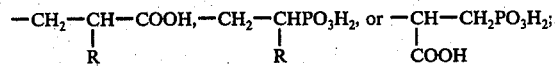

and
(c) cyclohexane-1,2,3,4,5,6-hexacarboxylic acid; and
(d) the pharmacologically harmless salts of the above compounds.

When the calcitonin is administered by injection, the dose of calcitonin is in an amount sufficient to provide from 0.01 to 20 International Medical Research Council units per kilogram of body weight.

When both the components are administered by injection, the ratio of calcitonin to adjuvant is generally between 1:1 and 10:1, if the amount of calcitonin is expressed in MRC units and the amount of adjuvant in mg.

When the calcitonin is administered by injection and the adjuvant is aministered orally, the ratio of calcitonin to adjuvant is generally between 1:10 and 1:1, if the amount of calcitonin is expressed in MRC units and the amount of adjuvant in mg.

The calcitonins which are suitable for use in the invention comprise synthetic and natural human calcitonin and the natural calcitonin of pigs, cattle and salmon and synthetic calcitonins of those latter types. Natural calcitonins, the biological effectiveness of which has been modified by replacement of individual amino acid groups in their peptide chain (which consists of 32 amino acid units) can be used equally well. Certain of these modified calcitonins are commercially available.

Aminophosphonic acids of formula (I) can be prepared by reacting shorter-chained substituted or unsubstituted dicarboxylic amides, α,ω-dinitriles, or an appropriate imide (for example succinimide) with phosphonylating agents, like phosphorus trihalides for example $PCl_3$ or $H_3PO_3$, followed by acid hydrolysis.

Diaminoalkane-tetraphosphonic acids of formula (II) can be prepared by reacting the longer chain, substituted or unsubstituted dicarboxylic diamides or α,ω-dinitriles with phosphonylating agents, like phosphorus trihalides or $H_3BO_3$, followed by acid hydrolysis.

Pyrrolidone-5,5-diphosphonic acids of formula (III) are preferably prepared by highly alkaline hydrolysis of amino-phosphonic acids of formula I wherein $n$ is 3.

Piperidone-6,6-diphosphonic acids of formula (IV) are preferably prepared by highly alkaline hydrolysis of aminophosphonic acids of formula I wherein $n$ is 3.

Azacycloalkane-2,2-diphosphonic acids of formula (V) can be prepared by reacting lactams with phosphonylating agents like phosphorus trihalides or $H_3PO_3$.

3-Amino-1-hydroxypropane-1,1-diphosphonic acids of formula (VI) can be prepared by phosphonylating β-alanine or β-alanine alkylated on the nitrogen atom with phosphorus trihalides or $H_3PO_3$.

The above-mentioned phosphonic acids can be converted to partial or complete salt form by neutralization in aqueous solution with an appropriate amount of the indicated base.

The pharmacologically harmless salts of the above compounds of acidic character (e.g., sodium, potassium, magnesium, zinc, ammonium and substituted ammonium salts like the mono, di, or triethanol ammonium salts) are suitable for use in the compositions of the present invention instead of or in combination with the above-mentioned aminophosphonic acids. Both the partial salts (i.e. salts in which only a part of the acid protons is substituted by other cations), and the complete salts can be used, but the partial salts which provide a substantially neutral or mildly alkaline pH in aqueous solution (i.e., a pH in the range of 5 to 9) are preferred. Mixtures of the above-mentioned salts can likewise be used.

The required amount of the adjuvant of the present invention to be administered depends on the disease to be treated, the severity of the disease, and the duration of the treatment. Single doses can be tolerated between 0.1 mg. and 200 mg. per kilogram of body weight. Doses between 0.5 mg. and 30 mg/kg. are preferable and up to 4 doses within this range can be administered per day. The higher doses are administered orally because absorption of the agent by the body is incomplete when they are administered in this way. Repeated administrations of more than 100 mg/kg of the adjuvant can cause toxic symptoms and should be avoided, even when the compound is administered per os.

The following table shows suggested oral doses of the adjuvants for different diseases:

| Disease | Oral Dose Up to 4 Times Daily |
|---|---|
| Paget's disease | 1 to 20 mg./kg. of body weight |
| Osteoporosis | 0.5 to 10 |
| Hypercalcemia | 0.5 to 20 |

A higher initial dose may be necessary, for example, up to twice the amount of the normal or maintenance dose shown above.

The adjuvants can also be administered parenterally in aqueous solution by subcutaneous, intradermal, intermuscular, intraperitoneal and intravenous injection, preferably in the form of their neutral or mildly alkaline salts. The following doses are prepared when the adjuvant is administered by injection.

| Method | Parentertal Dose Up to 4 Times Daily |
|---|---|
| Subcutaneous | 0.1 to 10 mg/kg of body weight |
| Intradermal | 0.1 to 10 |
| Intramuscular | 0.05 to 5 |
| Intravenous | 0.05 to 5 |
| Intraperitoneal | 0.05 to 5 |

Oral administration is preferred, however. The adjuvants can be present in the form of solutions (which preferably have a mildly alkaline pH), in which event the compounds are present in the form of their partial salts. For oral administration the compounds are provided in convenient dose units, e.g. in the form of capsules, dragees, tablets, or pills alone or in admixture with diluents, carriers, flavors, colorants, etc.

Calcitonin is preferably administered in aqueous solution by subcutaneous, intradermal, intramuscular, intraperitoneal or intravenous injection.

The following doses are preferred when the calcitonin is administered by injection:

| Method of Injection | Dose (units per kilogram of body weight per day) |
|---|---|
| Subcutaneous | 0.02 to 20 MRC |
| Intradermal | 0.02 to 20 |
| Intramuscular | 0.01 to 10 |
| Intraperitoneal | 0.01 to 10 |
| Intravenous | 0.01 to 10 |

The international MRC (Medical Research Council) unit for calcitonin is defined as 1/10 of the amount of calcitonin which causes the concentrates of calcium in the blood plasma of a rat weighing 150 g. to decrease by 10% in the first hour after injection intravenously.

Synthetic human calcitonin and pig calcitonin have activities of about 100 MRC units per mg. The activity of natural salmon calcitonin is about 3,000 to 4,000 MRC units per mg.

Phosphonoalkane-polycarboxylic acids suitable for use in the present invention are listed in the following table.

TABLE 1

Phosphono-ethane-1,2-dicarboxylic acid
1-Phosphono-propane-1,2-dicarboxylic acid
1-Phosphono-pentane-1,2-dicarboxylic acid
2-Phosphono-propane-2,3-dicarboxylic acid
2-Phosphono-pentane-1,2-dicarboxylic acid
2-Phosphono-butane-2,3-dicarboxylic acid
2-Phosphono-pentane-2,3-dicarboxylic acid
4-Phosphono-octane-4,5-dicarboxylic acid
2-Phosphono-butane-1,2,4-tricarboxylic acid
2-Phosphono-pentane-1,2,4-tricarboxylic acid
2-Phosphono-hexane-1,2,4-tricarboxylic acid
2-Phosphono-heptane-1,2,4-tricarboxylic acid
3-Phosphono-pentane-2,3,5-tricarboxylic acid
3-Phosphono-heptane-1,3,4-tricarboxylic acid
3-Phosphono-hexane-2,3,5-tricarboxylic acid
4-Phosphono-octane-3,4,6-tricarboxylic acid
5-Phosphono-nonane-4,5,7-tricarboxylic acid
3-Phosphono-octane-2,3,5-tricarboxylic acid
1,3-Diphosphono-butane-3,4-dicarboxylic acid
2,4-Diphosphonopentane-4,5-dicarboxylic acid
3,5-Diphosphonohexane-5,6-dicarboxylic acid
2,4-Diphosphonoheptane-1,2-dicarboxylic acid
1,3-Diphosphonopentane-3,4-dicarboxylic acid
1,3-Diphosphonohexane-3,4-dicarboxylic acid
2,4-Diphosphonohexane-4,5-dicarboxylic acid
3,5-Diphosphonooctane-5,6-dicarboxylic acid
3,5-Diphosphonononane-5,6-dicarboxylic acid
3,5-Diphosphonooctane-2,3-dicarboxylic acid
1,3-Diphosphonobutane-2,3,4-tricarboxylic acid
1,3-Diphosphono-pentane-2,3,4-tricarboxylic acid
1,3-Diphosphono-heptane-2,3,4-tricarboxylic acid
1-Phosphono-propane-1,2,3-tricarboxylic acid
2-Phosphono-butane-2,3,4-tricarboxylic acid
3-Phosphono-pentane-1,2,3-tricarboxylic acid
3-Phosphono-hexane-1,2,3-tricarboxylic acid
4-Phosphono-heptane-2,3,4-tricarboxylic acid
2-Phosphono-hexane-2,3,4-tricarboxylic acid
4-Phosphono-nonane-4,5,6-tricarboxylic acid
2-Phosphono-pentane-2,3,4-tricarboxylic acid
3-Phosphono-heptane-3,4,5-tricarboxylic acid
1-Phosphono-2-methyl-propane-1,2,3-tricarboxylic acid
2-Phosphono-3-ethyl-butane-2,3,4-tricarboxylic acid
3-Phosphono-4-methyl-pentane-3,4,5-tricarboxylic acid
4-Phosphono-5-propyl-hexane-4,5,6-tricarboxylic acid
2-Phosphono-3-methyl-hexane-2,3,4-tricarboxylic acid
4-Phosphono-5-methyl-nonane-4,5,6-tricarboxylic acid
1-Phosphono-2-methyl-pentane-1,2,3-tricarboxylic acid
2-Phosphono-3-methyl-pentane-2,3,4-tricarboxylic acid
3-Phosphono-4-ethyl-heptane-3,4,5-tricarboxylic acid
1,1-Diphosphono-propane-2,3-dicarboxylic acid
2,2-Diphosphono-butane-3,4-dicarboxylic acid
3,3-Diphosphono-pentane-4,5-dicarboxylic acid
3,3-Diphosphono-hexane-1,2-dicarboxylic acid
2,2-Diphosphono-pentane-3,4-dicarboxylic acid
4,4-Diphosphono-heptane-2,3-dicarboxylic acid
1,1-Diphosphono-pentane-2,3-dicarboxylic acid
3,3-Diphosphono-heptane-4,5-dicarboxylic acid
1,1-Diphosphono-2-methyl-propane-2,3-dicarboxylic acid
2,2-Diphosphono-3-methyl-butane-3,4-dicarboxylic acid
2,2-Diphosphono-3-methyl-pentane-3,4-dicarboxylic acid
3,3-Diphosphono-4-ethyl-heptane-4,5-dicarboxylic acid 2,2-Diphosphono-3-propyl-heptane-3,4-dicarboxylic acid
1-Phosphono-butane-2,3,4-tricarboxylic acid
1-Phosphono-pentane-2,3,4-tricarboxylic acid
1-Phosphono-3-methyl-pentane-2,3,4-tricarboxylic acid
1-Phosphono-3-methyl-heptane-2,3,4-tricarboxylic acid
1-Phosphono-3-propyl-hexane-2,3,4-tricarboxylic acid
1-Phosphono-3-methyl-butane-2,3,4-tricarboxylic acid
1-Phosphono-3-propyl butane-2,3,4-tricarboxylic acid The above-mentioned acids can also be employed in the form of their full or partial salts with water-soluble physiologically harmless cations. Suitable cations include the sodium, potassium, magnesium, and ammonium, as well as ammonium substituted by alkanol groups in the form of mono-, di-, and triethanolammonium cations. Both the partial salts, in which only a part of the acid protons is substituted by other cations, and the complete salts can be used, but partial salts which provide a substantially neutral to slightly alkaline pH (i.e., pH in the range of 5 to 9) when dissolved in water are preferred. Mixtures of the above-mentioned salts can likewise be used.

Particularly good results are obtained when calcitonin is administered together with the sodium partial salts of the following carboxyphosphonates:

1. 1,2-Phosphono-ethane-dicarboxylic acid (2:1 by weight mixture of the disodium and trisodium salts).
2. 2-Phosphono-2,3-propane-dicarboxylic acid (2:1 by weight mixture of the disodium and trisodium salts).
3. 2-Phosphono-1,2,4-butane-tricarboxylic acid (trisodium salt).

The phosphonealkane polycarboxylic acids used are prepared according to known methods.

1-Phosphono-1,2-ethane-dicarboxylic acid can be prepared by reaction of maleic ester (diethyl maleate) with diethyl phosphite in the presence of sodium alcoholate followed by acid saponification of the ester. 2-Phosphono-2,3-propane dicarboxylic acid can be obtained in the same manner with addition of the step of reacting the mixture with methyl chloride before the saponification step.

1-Phosphono-1,2,3-propane-tricarboxylic acid can be prepared by reacting maleic ester with phosphonoacetic ester (ethyl phosphonoacetate) in the presence of sodium alcoholate and subsequent saponification of the ester obtained. 1-Phosphono-2,3,4-butane tricarboxylic-acid can also be obtained by reacting dimethyl phosphite with 1-butane-2,3,4-tricarboxylic acid in the presence of sodium alcoholate followed by saponification of the ester thus obtained to the acid.

By reacting a lower alkyl methane-diphosphonate with a lower alkyl maleate in the presence of sodium alcoholate an ester is obtained which is converted by acid hydrolysis into 1,1-diphosphono-2,3-propane dicarboxylic acid.

2-Phosphono-2,3,4-butane-tricarboxylic acid can be obtained by reacting the methyl ester of α-diethyl phosphonopropionic acid with diethyl maleate in the presence of sodium alcoholate followed by saponification of the ester obtained.

The production of 2,2-diphosphono-3,4-butane-dicarboxylic acid is effected by reacting diethyl maleate with ethyl ethane-1,1-diphosphonate in the presence of sodium alcoholate followed by acid saponification of the product obtained.

The other phosphonalkane polycarboxylic acids are obtained by an analogous method where particularly ethyl citraconate is used instead of diethyl maleate.

The production of the corresponding water-soluble salts can be effected by complete or partial neutralization of the acids with water-soluble inorganic bases e.g. NaOH, KOH, and $NH_4OH$ or with alkanolamines, as well as with alkali metal carbonates.

Cyclohexane-1,2,3,4,5,6-hexacarboxylic acid can be prepared by partially hydrogenating phthalic acid to form 3,5-cyclohexadiene-1,2-dicarboxylic acid, reacting the product with maleic anhydride to form bicyclo-2,2,2, 7-octane-2,3,5,6-tetracarboxylic acid, and catalytically oxidizing this intermediate.

Such a method is described as French Pat. No. 1,563,486. The acid can be converted in known manner by complete or partial neutralization into the desired salts.

For pharmaceutical applications, instead of the free acids the pharmacologically harmless salts thereof can be used, e.g., the sodium, potassium, magnesium, zinc, ammonium and substituted ammonium salts (e.g., the mono, di, or triethanol ammonium salts). Both the partial salts (in which only a part of the acid protons present in the acid substituent is substituted by other cations) and the complete salts can be used, but partial salts which provide a substantially neutral or slightly alkaline pH in aqueous solution (pH 5-9) are preferred. Mixtures of the above-mentioned salts can likewise be used.

Cyclohexanehexacarboxylic acid in the form of its neutral salts can also be administered parenterally in aqueous solution by subcutaneous, intradermal, intramuscular, intrapertioneal or intravenous injection.

The invention is illustrated by the examples which follows. These examples provide illustrations of the invention and are not to be construed in limitation thereof.

EXAMPLE 1

The following illustrates the treatment of a case of Paget's disease by subcutaneous injection of calcitonin and oral administration of a substantially neutral salt of an aminophosphonate adjuvant in weight ratio of 1:20, the material being administered twice daily, the materials being administered respectively at the rate of 0.5 mg. and 5 mg. per kilogram of body weight per day.

A patient weighing about 70 kg. who suffered from Paget's disease, and whose blood serum showed greatly increased alkaline phosphatases and whose urine showed greatly increased hydroxyproline values, was treated twice daily with 0.5 mg. of synthetic human calcitonin (administered by subcutaneous injection) at rate of 1.4 MRC units/kg. of body weight per day and 350 mg. of disodium 3-amino-1-hydroxypropane-1,1-diphosphonate (administered orally). The aminodiphosphonate was administered as a dry powder contained in an ordinary capsule with additional components as follows:

| Component | Mg. per Capsule |
| --- | --- |
| Disodium 3-amino-hydroxy-propane-1,1-diphosphonate | 350.0 |
| Starch | 47.5 |
| Sodium lauryl sulfate | 2.5 |

After 4 weeks of the therapy, the biochemical control values had dropped considerably. After four months of the therapy the blood serum alkaline phosphatase and the urine hydroxyproline values were normal. The histological condition of the bones was likewise normal, and in particular there was no unmineralized osteoid tissue.

Similar results are obtained when the disodium salt of 2,7-dioxo-2-hydroxy-3-amino-3-phosphono-1,2-azaphosphacycloheptane or the disodium salt of azacycloheptane-2,2-diphosphonic acid is used. Similar results are also obtained if the synthetic human calcitonin is replaced by equivalent amounts of other calcitonins.

EXAMPLE 2

The following illustrates the treatment of a case of Paget's disease by subcutaneous administration of calcitonin and intravenous administration of a substantially neutral salt of an aminophosphonic acid, the materials being administered twice daily.

A patient weighing about 55 kg. who suffered from Paget's disease and showed greatly increased blood serum phosphates and urine hydroxyproline values was treated twice daily with 0.2 mg. of synthetic human calcitonin (administered subcutaneously (equivalent to 0.7 MRC units per kilogram of body weight per day) and 25 mg. of the disodium salt of 2,7-dioxo-2-hydroxy-3-amino-3-phosphono-1,2-azaphosphacycloheptane (administered intravenously.) After a few weeks of treatment the biochemical values had dropped considerably and the bone aches disappeared. After a few months of the treatment the condition of the patient was almost normal. In particular, histological examination revealed no unmineralized osteoid tissue.

Similar results are obtained when the disodium salts of 3-amino-1-hydroxypropane-1,1-diphosphonic acid or of azacycloheptane-2,2-diphosphonic acid are used. Instead of the synthetic human calcitonin, equivalent amounts of other calcitonins can be used.

EXAMPLE 3

The following illustrates the preparation of tablets of the adjuvant component in unit dose form suitable for oral administration, and the use thereof in the treatment of a patient suffering from osteoporosis.

Tablets are produced in conventional manner by compacting the following mixture.

| Components | Mg. per Tablet |
| --- | --- |
| Disodium azacycloheptane-2,2-diphosphonate | 250.0 |
| Lactone | 80.0 |
| Starch | 19.0 |
| Magnesium stearate | 1.0 |

With oral administration of one tablet twice daily and daily injection of 0.02 mg. of synthetic salmon calcitonin (80 MRC units/kg. of body weight) administered intramuscularly, loss of bone substance is considerably reduced in osteoporosis patients of about 50–70 kg. of body weight. During the period running from the start of the therapy for one year no spontaneous fractures were observed.

Similar results were obtained with the administration of tablets which were formulated in a similar manner, but which respectively contained, instead of the disodium salt of the azacycloheptane-2,2-diphosphonic acid, (a) the disodium salt of 3-amino-1-hydroxypropane-1,1-diphosphonic acid and (b) 2,7-dioxo-2-hydroxy-3-amino-3-phosphono-1,2-azaphosphacycloheptane.

Other pharmaceutically acceptable tabletting aids than lactose, starch and magnesium stearate can be present without impairing the effectiveness of the phosphonic acid.

Similar results are also obtained when the synthetic salmon calcitonin is replaced by equivalent amounts of other calcitonins.

EXAMPLE 4

The following illustrates the preparation of a dragee containing an adjuvant of the present invention and the treatment therewith in conjunction with calcitonin of a patient suffering from hypocalcemia.

Dragees are produced in conventional manner with a core which consists of the following components.

| Components | Mg. per Dragee |
| --- | --- |
| Disodium 3-amino-1-hydroxypropane 1,1-diphosphonate | 250.0 |
| Lactose | 60.0 |
| Starch | 12.0 |
| Carboxymethyl cellulose | 18.0 |
| Talcum | 8.0 |
| Calcium stearate | 2 |

With oral administration of one dragee twice daily and with daily injection of 0.75 mg. of synthetic pig calcitonin (75 MRC units subcutaneously) a drop in the calcium ion content of the blood serum is observed after a few hours in a hypercalcemia patient weighing 70 kg. In the course of a few days the serum calcium value again attains the normal value in most patients.

Similar results are obtained when the disodium salts of 2,7-dioxo-2-hydroxy-3-amino-3-phosphono-1,2-azaphosphacycloheptane and of azacycloheptane-2,2-diphosphonic acid are respectively used.

Similar results are also obtained when the pig calcitonin is replaced with equivalent amounts of other calcitonins.

EXAMPLE 5

The following illustrates the treatment of a patient suffering from Paget's disease by subcutaneous administration of calcitonin and by administration of an adjuvant in powdered encapsulated form.

A patient weighing about 70 kg. who suffered from Paget's disease and who showed greatly increased phosphatase and urine hydroxyproline values, was treated twice daily with 0.5 mg. of synthetic human calcitonin administered subcutaneously (equivalent of 1.4 MRC units per kilogram of body weight per day) and 350 mg. of 2-phosphonopropane-2,3 dicarboxylic acid (2:1 mixture of the disodium and trisodium salts) administered orally. The carboxyphosphonate is administered in admixture with carrier material in capsules of the following composition.

| Components | Mg. per Capsule |
| --- | --- |
| 2-Phosphono-propane-2,3 dicarboxylic acid (2:1 mixture of disodium: trisodium salts) | 350.0 |
| Starch | 47.5 |
| Sodium lauryl sulfate | 2.5 |

After 4 weeks of therapy the biochemical control values have dropped considerably. The bone aches have completely disappeared. After four months the alkaline phosphatase and the urine-hydroxyproline values are normal. The histological finding is also normal, in particular there is no unmineralized osteoid tissue.

Similar results are obtained when (a) a 2:1 mixture of the disodium and trisodium salts of phosphonoethane-1,2-dicarboxylic acid and (b) trisodium 2-phosphono-propane-2,3-dicarboxylate are used. Instead of synthetic human calcitonin can also be used equivalent amounts of other calcitonins.

EXAMPLE 6

A patient weighing about 55 kg. who suffered from Paget's disease and who showed greatly increased blood serum alkaline phosphatase and urine hydroxyproline values was treated twice daily with 0.2 mg. of synthetic human calcitonin (equivalent to 0.7 MRC units per kilogram of body weight per day) administered subcutaneously and 25 mg. of trisodium 2-phosphonobutane-1,2,4-tricarboxylate (administered intravenously). After a few weeks the biochemical control values of the patient dropped considerably and bone aches disappeared. After a few months the condition of the patient was almost normal. In particular, the histological findings show no unmineralized osteoid tissue.

Similar results are obtained when 2:1 mixtures of the disodium and trisodium salts of phosphonoethane-1,2-dicarboxylic acid and 2-phosphono-propane-2,3-dicarboxylic acid are used. Instead of the synthetic human calcitonin can also be used equivalent amounts of other calcitonins.

EXAMPLE 7

The following illustrates the treatment of a case of Paget's disease by subcutaneous administration of calcitonin and oral administration of the adjuvant.

Unit dose tablets of the following composition are produced by tabletting a homogenous mixture of the following materials.

| Components | Mg. per Tablet |
| --- | --- |
| Trisodium 2-phosphono-butane 1,2,4-tricarboxylate | 250.0 |
| Lactose | 80.0 |
| Starch | 19.0 |
| Magnesium stearate | 1.0 |

With oral administration twice daily and daily subcutaneous injection of 0.02 mg. of synthetic salmon calcitonin (80 MCR units per kilogram of body weight per day administered intramuscularly), loss of bone matter is considerably reduced in patients of about 50 – 70 kg. body weight. In a period of one year after the start of the therapy no spontaneous fractures are observed.

Similar results are obtained with the administration of tablets similarly made but which respectively contain instead of trisodium salt of 2-phosphono-butane-1,2,4 tricarboxylic acid (a) a mixture of the disodium and trisodium salts in 2:1 ratio of phosphono-ethane-1,2-dicarboxylic acid and (b) 2-phosphono-propane-2,3-carboxylic acid.

Similar results are also obtained when the synthetic salmon calcitonin is replaced by corresponding doses of other calcitonins.

EXAMPLE 8

In a known manner are produced dragees the core of which consists of a tablet of the following materials.

| Components | Mg. per Dragee |
| --- | --- |
| Phosphonoethane-1,2-dicarboxylic acid (2:1 mixture of disodium and trisodium salts) | 250.0 |
| Lactose | 60.0 |
| Starch | 12.0 |
| Carboxymethyl cellulose | 18.0 |
| Talcum | 8.0 |
| Calcium stearate | 2.0 |

With oral administration of one dragee twice daily and daily injection of 0.75 mg. of synthetic pig calcitonin (75 units per kilogram of body weight, administrated subcutaneously) a drop of the calcium level is observed after a few hours in a hypercalcemia patient weighing 70 kg.

In the course of a few days the serum calcium value again attains in most patients the normal value.

Similar results are obtained when trisodium 2-phosphono-butane,1,2,4-tricarboxylate or a mixture of the disodium and trisodium salts (ratio 2:1) of 2-phosphono-propane-2,3-dicarboxylic acid is used.

Similar results are also obtained with equivalent amounts of other calcitonins.

EXAMPLE 9

A patient of about 70 kg. who suffered from Paget's disease and showed greatly increased alkaline phosphatase and urine hydroxyproline values, was treated twice daily with 0.5 mg. of synthetic human calcitonin (equivalent to 1.4 MRC units per kilogram of body weight per day) and 350 mg. of trisodium cyclohexane-1,2,3,4,5,6-hexacarboxylate (administered orally) in the form of capsules of the following composition:

| Components | Mg. per Capsule |
| --- | --- |
| Trisodium cyclohexane-1,2,3,4,5,6-hexa-carboxylate | 350.0 |
| Starch | 47.5 |
| Sodium lauryl sulfate | 2.5 |

After 4 weeks of therapy, the biochemical control values were considerably lower than at the start, and the bone aches had completely disappeared. After 4 months the blood serum alkaline phosphatase and the urine hydroxyproline values are normal. The histological finding is also normal. In particular there is no unmineralized osteoid tissue.

Similar results are obtained when the synthetic human calcitonin is replaced by corresponding doses of other calcitonins.

EXAMPLE 10

A patient of about 55 kg. who suffered from Paget's disease and who showed greatly increased blood serum, alkaline phosphatase and urine hydroxyproline values was treated twice daily by administration of 0.2 mg. of synthetic human calcitonin (equivalent to 0.7 MRC units per kilogram of body weight per day) and 25 mg. of trisodium cyclohexane 1,2,3,4,5,6-hexacarboxyate administered intravenously. After a few weeks the biochemical control values were considerably lower and the bone aches had disappeared. After a few months the condition of the patient was greatly normalized, in particular the histological findings show no unmineralized osteoid tissue.

Similar results are obtained when the synthetic human calcitonin is replaced by corresponding doses of other calcitonins.

EXAMPLE 11

Unit doses of an equivalent according to the present invention are produced by tabletting the following mixture.

| Component | Mg. per Tablet |
|---|---|
| Trisodium cyclohexane-1,2,3,4,5,6-hexacarboxylate | 250.0 |
| Lactose | 80.0 |
| Starch | 19.0 |
| Magnesium stearate | 1.0 |

With oral administration of one tablet of the adjuvant twice daily (total 500 mg.) and daily injection of 0.02 mg. of synthetic salmon calcitonin (80 MRC units per kilogram of body weight per day, administered intramuscularly), loss of bone is considerably reduced in osteoporosis patients of about 50 - 70 kg. body weight. In a period of one year from the start of the therapy no spontaneous fractures were observed.

Similar results are also obtained when the synthetic salmon calcitonin is replaced by therapeutically equivalent amounts of other calcitonins.

EXAMPLE 12

Dragees containing an acid adjuvant suitable for use in the present invention are produced in conventional manner, the core of which is a tablet of the following composition.

| Components | Mg. per Dragee |
|---|---|
| Cyclohexane-1,2,3,4,5,6-hexacarboxylic acid | 250.0 |
| Lactose | 60.0 |
| Starch | 12.0 |
| Carboxymethyl cellulose | 18.0 |
| Talcum | 8.0 |
| Calcium stearate | 2 |

With oral administration of two tablets of the adjuvant twice daily (total 500 mg.) and daily injection of 0.75 mg. of synthetic pig calcitonin (75 MRC units per kilogram of body weight per day, administered subcutaneously) a drop in the calcium level of the blood serum is observed after a few hours in a hypercalcemic patient of 70 kg. of body weight. In the course of a few days the serum calcium value becomes normal value in most patients.

Similar results are also obtained when the pig calcitonin is replaced by therapeutically equivalent amounts of other calcitonins.

EXAMPLE 13

The following illustrates the preparation of a pharmaceutical preparation of a calcitonin and a phosphonate as a single injectable solution and treatment of Paget's disease therewith.

For the production of pharmaceutical preparations in form of injectable solutions, the known methods of preparation were followed to produce a solution having an effective dosage as follows.

| Component | Dosage Unit |
|---|---|
| Disodium-3-amino-1-hydroxy-propane-1,1-diphosphonate | 30 mg./ml. |
| Salmon calcitonin (spec. activity 3000 MRC U/mg.) | 0.01 mg./ml. |

The resulting solution has a pH value of 7.4 and is adjusted with sodium chloride to plasma ionic strength. A patient suffering from morbus paget, weighing 60 kg, is treated with intramuscular injections of one ml./day of this pharmaceutical solution for several months. After 6 weeks a noticeable decrease in the biochemical parameters "serum alkaline phosphatase" and "urine hydroxyproline" is observed. Simultaneously, bone pain disappears. After four months of treatment, the state of the patient has normalized. Bone biopsies show no sign of unmineralized bone tissue.

Similar results are obtained using solutions containing combinations of salmon, human or bovine calcitonin and either of two diphosphonates (disodium-azacycloheptane-2,2-diphosphonate or the disodium salt and of 2,7-dioxo-2-hydroxy-3-amino-3-phosphono-1,2-azaphosphacycloheptane).

EXAMPLE 14

The following illustrates the preparation of a similar pharmaceutically acceptable preparation wherein the calcitonin is human calcitonin.

For the production of pharmaceutical preparations in form of injectable aqueous solutions, the known methods of preparation were followed to produce a solution having an effective dosage unit as follows.

| Component | Dosage Unit |
|---|---|
| Trisodium-2-phosphono-butane-1,2,4-tricarboxylate | 50 mg./ml. |
| Human calcitonin (Spec. activity 100 MRC U/mg.) | 0.25 mg./ml. |

The resulting solution has a pH value of 7.4 and is adjusted with sodium chloride to plasma ionic strength. A patient suffering from osteoporosis, weighing approximately 50 kg., is treated with intravenous injections of one ml./day of this pharmaceutical preparation for one year. The rate of bone loss in the patient is greatly reduced, and within the period of treatment no further spontaneous bone fractures were observed.

Similar results are obtained using solutions containing combinations of salmon, human or bovine calcitonin and either of two phosphono-carboxylates(phosphonoethane-1,2-dicarboxylate and phosphonopropane-2,3-dicarboxylate) as 2:1 mixtures of the di- and trisodium salts respectively.

EXAMPLE 15

The following illustrates the preparation of a similar pharmaceutically acceptable preparation wherein the calcitonin is bovine calcitonin.

For the production of pharmaceutical preparations in the form of injectable aqueous solutions, the known methods of preparation were followed to produce a solution having an effective dosage unit as follows.

| Component | Dosage Unit |
|---|---|
| Cyclohexane-1,2,3,4,5,6-hexacarboxylic-acid, trisodium salt | 70 mg./ml. |
| Bovine calcitonin (spec. activity 140 MRC U/mg.) | 0.5 mg./ml. |

The resulting solution has a pH value of 7.4 and is adjusted with sodium chloride to plasma ionic strength.

In a group of three patients suffering from hypercalcemia weighing 72, 60 and 58 kg. respectively, each patient is treated by daily subcutaneous injections of one ml. of this pharmaceutical preparation. After a few hours a reduction in the plasma calcium level is observed, and within a few days, plasma calcium levels have returned to normal.

Similar results are obtained using solutions containing combinations of either salmon or synthetic human calcitonin with trisodium cyclohexanehexacarboxylate.

We claim:

1. A composition for inhibiting pathological solubilization of bone calcium in mammals, comprising (A) a water-soluble calcitonin and (B) a water-soluble pharmaceutically acceptable organic adjuvant compound effective against Paget's disease, said compound containing at least two acidic groups separated by not more than two carbon atoms, and being selected from the group consisting of cyclohexanehexacarboxylic acid, azacycloheptane-2,2-diphosphonic acid,2,7-dioxo-2-hydroxy-3-amino-3-phosphono-1,2-azaphosphacycloheptane, 3-amino-1-hydroxypropane-1,1-diphosphonic acid, phosphono-1,2-ethanedicarboxylic acid, 2-phosphono-2,3-propanedicarboxylic acid, 2-phosphonobutane-1,2,4-tricarboxylic acid, and the water-soluble salts thereof, the ratio of (A) to (B) being between 1:10 and 10:1, if the amount of (A) is expressed in MRC units and the amount of (B) in mg.

2. A composition according to claim 1 wherein the calcitonin is human calcitonin.

3. A composition according to claim 1 wherein the calcitonin is salmon calcitonin.

4. A composition according to claim 1 wherein the calcitonin is pig calcitonin.

5. A composition according to claim 1 wherein the adjuvant compound is cyclohexanehexacarboxylic acid or a pharmaceutically-acceptable water-soluble salt thereof.

6. A composition according to claim 1 wherein the adjuvant compound is 2,7-dioxo-2-hydroxy-3-amino-3-phosphono-1,2-azaphosphacycloheptane or a pharmaceutically-acceptable water-soluble salt thereof.

7. A composition according to claim 1 wherein the adjuvant compound is 3-amino-1-hydroxypropane-1,1-disphosphonic acid or a pharmaceutically-acceptable water-soluble salt thereof.

8. A composition according to claim 1 wherein the adjuvant compound is phosphono-1,2-ethanedicarboxylic acid or a pharmaceutically-acceptable water-soluble salt thereof.

9. A composition according to claim 1 wherein the adjuvant compound is 2-phosphono-2,3-propanedicarboxylic acid or a pharmaceutically-acceptable water-soluble salt thereof.

10. A composition according to claim 1 wherein the adjuvant compound is 2-phosphono-1,2,4-tricarboxylic acid or a pharmaceutically-acceptable water-soluble salt thereof.

11. A solution of a composition according to claim 1 in a physiologically acceptable injectable aqueous solvent.

12. A hermetically sealed, sterile daily dose package for dosing a mammal suffering from pathological increased calcium metabolism, which comprises at least one sterile ampoule containing a calcitonin in an amount sufficient to supply from 0.01 to 20 MRC units per kilogram of body weight and at least one tablet containing between 25 mg. and 400 mg. of a water-soluble organic adjuvant compound for inhibiting pathological solubilization of bone calcium in mammals, comprising (A) a water-soluble calcitonin and (B) a water-soluble pharmaceutically acceptable organic adjuvant compound effective against Paget's disease, said compound containing at least two acidic groups separated by not more than two carbon atoms and being selected from the group consisting of cyclohexanehexacarboxylic acid, azacycloheptane-2,2-diphosphonic acid, 2-7-dioxo-2hydroxy-3-amino-3-phosphono-1,2-azaphosphacycloheptane, 3-amino-1-hydroxypropane-1,1-diphosphonic acid, phosphono-1,2-ethanedicarboxylic acid, 2-phosphono-2,3-propanedicarboxylic acid, 2-phosphonobutane, 1,2,4-tricarboxylic acid, and the water-soluble salts thereof.

13. A daily dose package according to claim 12 containing four of said tablets.

14. A pharmaceutically acceptable injectable aqueous solution of (A) a water-soluble calcitonin and (B) a water-soluble pharmaceutically-acceptable adjuvant compound effective against Paget's disease, said adjuvant compound containing at least two acidic groups separated by not more than two carbon atoms and being selected from the group consisting of cyclohexanehexacarboxylic acid, azacycloheptane-2,2-diphosphonic acid, 2,7-dioxo-2-hydroxy-3-amino-3-phosphono-1,2-azaphosphacycloheptane, 3-amino-1-hydroxypropane-1,1-diphosphonic acid, phosphono-1,2-ethanedicarboxylic acid, 2-phosphono-2,3-propanedicarboxylic acid, 2-phosphonobutane-1,2,4-tricarboxylic acid, and the water-soluble salts thereof.

15. A solution according to claim 14 having a pH about 7.4.

16. A solution according to claim 14 containing dissolved sodium chloride in amount sufficient to adjust said solution to plasma ionic strength.

17. A method of inhibiting the pathological increased calcium metabolism in mammals, which comprises administering daily thereto, (A) a water-soluble calcitonin and (B) a water-soluble pharmaceutically-acceptable organic adjuvant compound effective against Paget's disease, said adjuvant compound containing at least two carbon atoms and being selected from the group consisting of cyclohexane-hexacarboxylic acid, azacycloheptane-2,2-diphosphonic acid, 2,7-dioxo-2-hydroxy-3-amino-3-phosphono-1,2-azaphosphacycloheptane, 3-amino-1-hydroxypropane-1,1-diphosphonic acid, phosphono-1,2-ethanedicarboxylic acid, 2-phosphono-2,3-propanedicarboxylic acid, 2-phosphonobutane-1,2,4-tricarboxylic acid, and the water-soluble salts thereof, the amount of said calcitonin being sufficient to supply between 0.01 and 20 Medical Research Council units thereof per kilogram of body weight per day and the amount of said adjuvant being from 0.05 to 30 mg./kg. of body weight per day.

18. A method according to claim 17 wherein the calcitonin is administered by injection into the body.

19. A method according to claim 17 wherein the adjuvant compound is administered orally at least 4 times a day.

20. A method according to claim 17 wherein compounds (A) and (B) are administered by injection as a single pharmaceutically acceptable aqueous solution.

21. A method according to claim 17 wherein the solution is administered once per day.

22. A method according to claim 17 wherein the solution has a pH of about 7.4.

23. A method according to claim 17 wherein the solution contains dissolved sodium chloride in amount to adjust said solution to plasma ionic strength.

24. A method according to claim 17 wherein the pathological increased metabolism is Paget's disease.

25. A method according to claim 17 wherein the pathological increased metabolism is hypercalcemia.

26. A method according to claim 17 wherein the pathological increased metabolism is osteoporosis.

27. The method of claim 17 wherein the organic adjuvant compound is administered per os in a dosage of 0.5 to 20 mg./kg. of body weight.

28. The method of claim 17 wherein the organic adjuvant compound is administered parenterally in a dosage of 0.05 to 10 mg./kg. of body weight.

* * * * *